United States Patent
Iino

(10) Patent No.: US 8,491,946 B2
(45) Date of Patent: Jul. 23, 2013

(54) ELASTASE INHIBITOR

(75) Inventor: Masato Iino, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 13/138,350

(22) PCT Filed: Aug. 6, 2010

(86) PCT No.: PCT/JP2010/063414
§ 371 (c)(1),
(2), (4) Date: Aug. 4, 2011

(87) PCT Pub. No.: WO2012/017555
PCT Pub. Date: Feb. 9, 2012

(65) Prior Publication Data
US 2012/0034260 A1    Feb. 9, 2012

(51) Int. Cl.
*A61K 36/73* (2006.01)
*A61K 36/06* (2006.01)
*A61K 38/48* (2006.01)
*A61P 17/00* (2006.01)

(52) U.S. Cl.
USPC ...... 424/765; 424/195.16; 424/777; 424/401; 514/20.4

(58) Field of Classification Search
None
See application file for complete search history.

(56) References Cited

U.S. PATENT DOCUMENTS

| | | | |
|---|---|---|---|
| 2002/0009472 | A1 | 1/2002 | Takekoshi et al. |
| 2005/0048105 | A1 * | 3/2005 | McNulty et al. |
| 2007/0134265 | A1 | 6/2007 | Takada et al. |

FOREIGN PATENT DOCUMENTS

| | | | |
|---|---|---|---|
| CN | 1161198 A | * | 10/1997 |
| JP | 2001-163794 A | | 6/2001 |
| JP | 2002-080321 A | | 3/2002 |
| JP | 2005-306831 A | | 11/2005 |
| KR | 2009132285 A | * | 12/2009 |
| WO | WO 2004/075621 A2 | | 9/2004 |

OTHER PUBLICATIONS

Johansson et al., "A Neutrophil Multitarget Functional Bioassay to Detect Anti-inflammatory Natural Products," J. Nat. Prod., 2002, 65(1):32-41.

* cited by examiner

*Primary Examiner* — Michele Flood
(74) *Attorney, Agent, or Firm* — Foley & Lardner LLP

(57) ABSTRACT

An elastase inhibitor that contains as active ingredients thereof raspberry extract and hydroxyproline, and optionally further contains yeast extract.

6 Claims, 2 Drawing Sheets

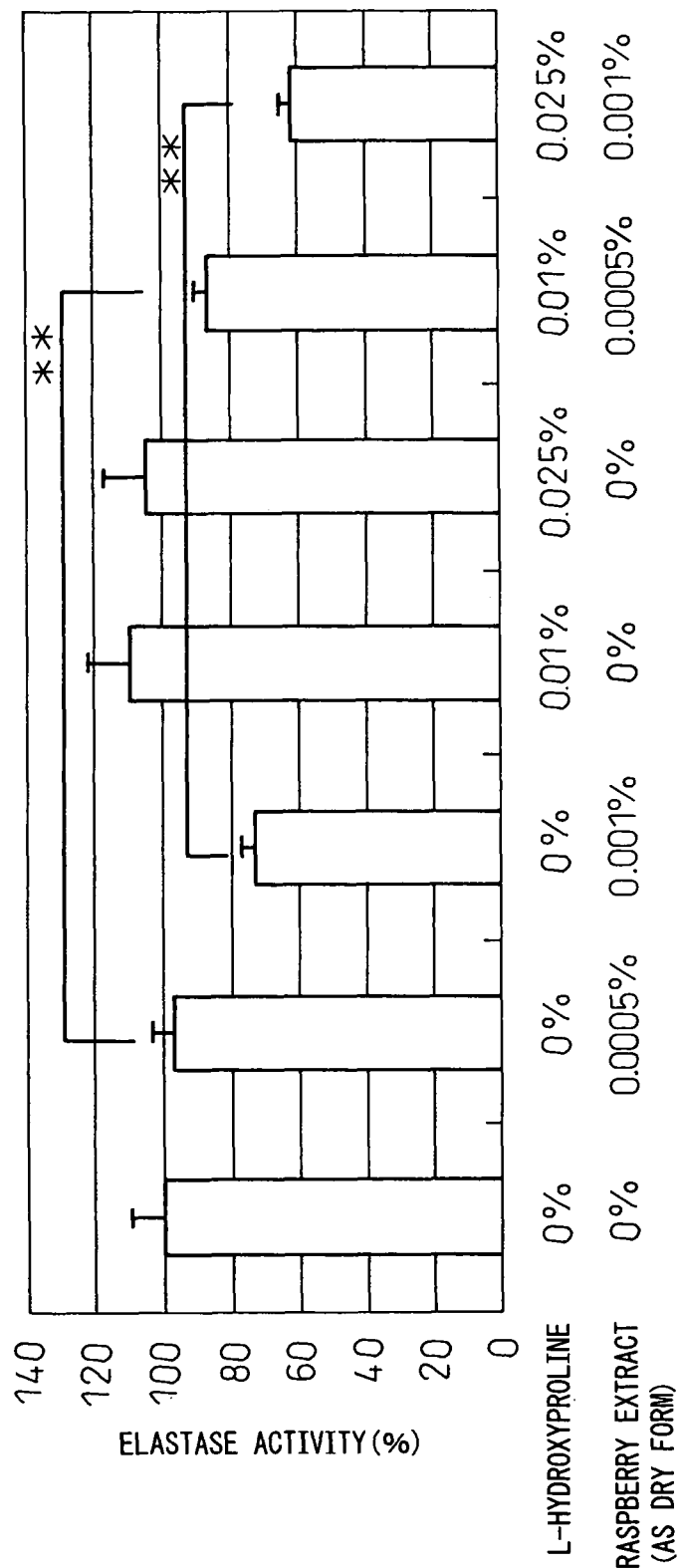

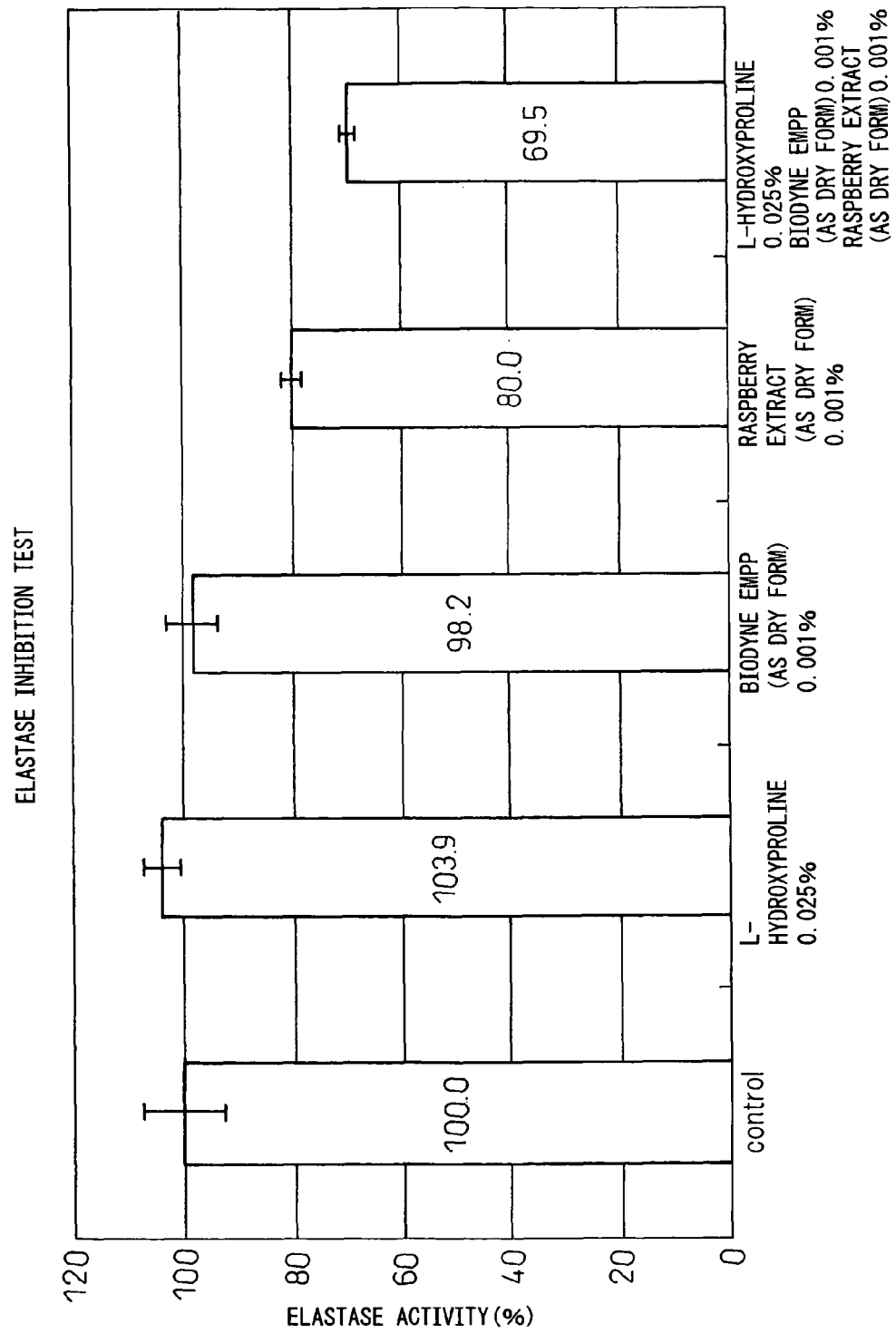

ELASTASE INHIBITOR

CROSS-REFERENCE TO RELATED APPLICATIONS

This application is a National Stage application of PCT/JP2010/063414, filed Aug. 6, 2010.

TECHNICAL FIELD

The present invention relates to an elastase inhibitor containing as active ingredients thereof a plant-derived component in the form of raspberry extract and hydroxyproline.

BACKGROUND ART

Although considerations have been given in the past to the need for anti-aging agents, since the mechanism and definition of aging have not been clarified, aging has typically been assessed by measuring moisture retention or skin resiliency as indicators of skin moistness or by visually observing skin color. However, research on aging has progressed in recent years, and age has been determined to be an important factor as a cause of skin aging in macroscopic terms, while the effects of drying, oxidation and sunlight (ultraviolet rays) and the like have also been indicated to be direct factors involved in skin aging. Known examples of specific phenomena associated with skin aging include reductions in collagen and elastin levels in the dermis, reductions in the levels of hyaluronic acid and other mucopolysaccharides, and cell damage caused by ultraviolet rays. Among these, although elastin contributes to tissue resiliency by mutually forming crosslinks, denaturation and destruction of elastin by excess expression of elastase, an enzyme that breaks down elastin, caused by exposure to ultraviolet rays and aging is thought to lead to a decrease in skin resiliency. Thus, inhibiting the action of elastase and preventing denaturation and destruction of elastin to impart resiliency and tightness to skin are important for preventing skin aging.

Although natural ingredients are preferable in the case of cosmetics and the like that are applied directly to the skin, known examples of natural elastase inhibitors include *Ficus religiosa* extract (Patent Document 1), *Saxifraga sarmentosa* extract (Patent Document 2), *Uncaria gambir* extract of the Madder family (Patent Document 3) and *Rhododendron simsii* extract of the Heath family (Patent Document 4), and external skin preparations containing these extracts have been shown to demonstrate improvement effects on wrinkles, fine wrinkles and in terms of skin tightness and sagging.

On the other hand, elastase inhibitors are also known to be useful in the treatment of disease in addition to their use as external skin preparations, and have been reported to be effective against diseases such as joint diseases including chronic rheumatoid arthritis and osteoarthritis, systemic inflammatory response syndrome, arteriosclerosis, acute lung disorders or acute respiratory distress syndrome.

Specific examples of such elastase inhibitors include pharmaceuticals such as urinary trypsin inhibitor, which is used for acute pancreatitis or acute circulatory failure (hemorrhagic shock), and the selective neutrophil elastase inhibitor, sivelestat sodium, which is effective for improving acute lung disorders associated with systemic inflammatory response syndrome. In this manner, although elastase inhibitors are used as therapeutics for the treatment of inflammatory diseases and the like, in consideration of safety, products composed mainly of natural ingredients rather than synthetic chemicals are preferable in this case as well.

Prior Art Documents
Patent Publications
 Patent Document 1: Japanese Unexamined Patent Publication No. H11-335230
 Patent Document 2: Japanese Unexamined Patent Publication No. H11-246386
 Patent Document 3: Japanese Unexamined Patent Publication No. H10-182414
 Patent Document 4: Japanese Unexamined Patent Publication No. 2009-191043

SUMMARY OF THE INVENTION

An object of the present invention is to provide an elastase inhibitor that is able to impart resiliency and tightness to skin by inhibiting elastase by using in an external preparation, and is useful as a disease therapeutic agent.

As a result of investigating the elastase inhibitory activity of various plant extracts, the inventor of the present invention found that a solvent extract of raspberry (*Rubus idacus* L.) has elastase inhibitory activity, and further that this inhibitory activity is synergistically enhanced by the addition of hydroxyproline, thereby leading to completion of the present invention.

Thus, the present application provides the following inventions:
(1) an elastase inhibitor containing as active ingredients thereof raspberry extract and hydroxyproline;
(2) the elastase inhibitor of (1), wherein the hydroxyproline is L-hydroxyproline;
(3) the elastase inhibitor of (1) or (2), further containing yeast extract;
(4) the elastase inhibitor of (3), wherein the yeast extract is prepared from yeast which has been cultured in a nutrient medium containing glycosaminoglycan, and which has been subjected to ultraviolet radiation, hydrogen peroxide treatment or both;
(5) an external skin preparation containing the elastase inhibitor of any of (1) to (4); and,
(6) the external skin preparation of (5) that is a cosmetic.

BRIEF DESCRIPTION OF THE DRAWINGS

FIG. 1 indicates elastase inhibitory activity of raspberry extract and hydroxyproline.
FIG. 2 indicates elastase inhibitory activity of various drugs and a mixture thereof.

BEST MODE FOR CARRYING OUT THE INVENTION

The following provides an explanation of embodiments of the present invention.

Raspberry (European strawberry) (*Rubus idacus* L.) is a plant belonging to the genus *Rubus* of the Rosaceae family. This plant is a deciduous shrub distributed among lowlands from Europe to western Asia and the east coast of the United States that produces white flowers around June. Fruit ripen around August to October, and first red and eventually become purplish black. The fruit of this plant are known as raspberries, and although the fruit have an elegant aroma and color, a delicious flavor and were once considered to be a typical fruit in times when few fruit were available, they are presently eaten by sprinkling with sugar or are processed into jam or syrup. Since the fruit contains pharmacological ingredients such as strongly astringent substances of sugars such as malic acid or citric acid, flavonoids having estrogen-like activity, various types of vitamins consisting mainly of vitamin C (ascorbic acid) and vitamin P (hesperidin, lutin) and sugars, in addition to being effective against dermatitis (rash, acne), it is also known to be used as a throat anti-inflammatory agent or anti-diarrheal agent.

Examples of forms of the raspberry extract used in the elastase inhibitor of the present invention are solvate extract, dilutions of the solvate extract, dried forms obtained by drying the solvate extract, and solution obtained by dissolving the dried form in a solvent. In addition, unrefined and refined products are also included.

The extraction solvent used in the present invention may be any one provided it is a solvent normally used for extraction, and water or organic solvents such as alcohols such as methanol, ethanol or 1,3-butyleneglycol, hydrous alcohols, acetone or ethyl acetate, can be used alone or in combination, with alcohols and hydrous alcohols being used preferably, and ethanol, 1,3-butyleneglycol, hydrous ethanol and hydrous 1,3-butyleneglycol being used particularly preferably. In addition, the solvent is preferably used at a temperature between room temperature and the boiling point of the solvent.

Although the preferable site of the aforementioned plant is the fruit, extracts from other sites can also be used.

Since the raspberry extract used in the present invention demonstrates superior elastase inhibitory action for human skin, an external skin preparation incorporating this plant extract is able to prevent skin aging and maintain the skin in a youthful and healthy state.

In the case of incorporating the elastase inhibitor of the present invention in an external preparation, the incorporated amount of raspberry extract as dry form is 0.000001 to 1% by weight, preferably 0.00001 to 0.1% by weight, more preferably 0.0001 to 0.01% by weight and most preferably about 0.001% by weight in the entire external preparation. If the incorporated amount is less than 0.000001% by weight, the effects as referred to in the present invention are not adequately demonstrated, while if the incorporated amount exceeds 1% by weight, it becomes difficult to formulate into a preparation, thereby making this undesirable.

Although the elastase inhibitor of the present invention may be composed only of raspberry extract, it preferably also contains hydroxyproline, and more preferably further contains yeast extract. The incorporation of hydroxyproline in particular makes it possible to synergistically enhance elastase inhibitory activity.

Hydroxyproline, and particularly L-hydroxyproline, is an amino acid characteristic to collagen. The amino acid sequence of collagen consists of -Gly-X—Y—, and at least one of the arbitrary amino acids of X and Y is composed of L-proline or L-hydroxyproline.

Hydroxyproline has various anti-aging effects on the skin, including production of collagen in fibroblasts 1), promotion of epidermal cell growth and moisturizing effects.

In the case of incorporating the elastase inhibitor of the present invention in an external preparation, the incorporated amount of hydroxyproline as dry form is 0.00001 to 10% by weight, preferably 0.0001 to 1% by weight, more preferably 0.001 to 0.1% by weight and most preferably about 0.025% by weight in the entire external preparation. If the incorporated amount is less than 0.00001% by weight, the effects as referred to in the present invention are not adequately demonstrated, while if the incorporated amount exceeds 10% by weight, it becomes difficult to formulate into a preparation, thereby making this undesirable.

The yeast extract in the present invention is preferably that which has been cultured in a nutrient medium containing glycosaminoglycan and has been subjected to ultraviolet radiation, hydrogen peroxide treatment or both. Cell protective components that protect cells from stress have been determined to be produced by culturing yeast in the presence of stress such as ultraviolet rays or hydrogen peroxide, and the response to stress can be enhanced by further adding nutrient peptones or glycosaminoglycans and the like to the medium at that time. An example of the production method thereof is described in U.S. Pat. No. 6,461,857. For example, yeast extract can be prepared by culturing Saccharomyces cerevisiae, which is a type of bread yeast, in a nutrient medium containing non-animal-derived glycosaminoglycan, adding a sub-lethal dose, such as about 0.1 to 2% by weight of the total weight of the culture, of hydrogen peroxide to the culture, optionally irradiating the culture with a sub-lethal dose of ultraviolet rays (by, for example, irradiating with UVA/UVB at an intensity of 31.5 mJ/cm$^2$) to carry out stress loading, and solubilizing the resulting culture by self-digestion or acid hydrolysis and the like, followed by drying, extracting with water and filtering. In addition, a yeast extract prepared from yeast that have been cultured in medium containing non-animal-derived glycosaminoglycan and subjected to ultraviolet radiation and hydrogen peroxide treatment is available commercially from Arch Personal Care Products L.P. under the trade name "Biodyne EMPP™".

In the case of incorporating the elastase inhibitor of the present invention in an external preparation, the incorporated amount of yeast extract as dry form is 0.000001 to 1% by weight, preferably 0.00001 to 0.1% by weight, more preferably 0.0001 to 0.01% by weight and most preferably 0.0005 to 0.005% by weight in the entire external preparation. If the incorporated amount is less than 0.000001% by weight, the effects as referred to in the present invention are not adequately demonstrated, while if the incorporated amount exceeds 1% by weight, it becomes difficult to formulate into a preparation, thereby making this undesirable.

In the case of using the elastase inhibitor of the present invention as an external preparation, components normally used in external skin preparations such as cosmetics or pharmaceuticals can be suitably combined and incorporated, examples of which include whitening agents, moisturizing agents, antioxidants, oily components, ultraviolet absorbers, surfactants, thickeners, alcohols, powder components, colorants, aqueous components, water and various types of skin nutrients.

In addition, metal chelating agents such as disodium edetate, trisodium edetate, sodium citrate, sodium polyphosphate, sodium metaphosphate or gluconic acid, drugs such as caffeine, tannin, verapamil, tranexamic acid and derivatives thereof, licorice extract, glabridin, hot water extracts of fire thorn (*Pyracantha fortuneana*), various herbal medicines, tocopherol acetate or glycyrrhizic acid and derivatives or salts thereof, other whitening agents such as vitamin C, magnesium ascorbyl phosphate, ascorbyl glucoside, albutin or kojic acid, and sugars such as glucose, fructose, mannose, sucrose or trehalose can also be suitably incorporated.

An external preparation containing the elastase inhibitor of the present invention can be widely used in cosmetics and quasi drugs, and particularly preferably in cosmetics, and a wide range of drug forms can be employed for the form thereof, examples of which include water-soluble liquids, solutions, emulsions, powders, oily liquids, gels, ointments, aerosols, water-oil bilayer systems and water-oil-powder trilayer systems. Namely, in the case of foundation cosmetics, the external preparation can be widely applied to the aforementioned drug forms in the form of, for example, a facial wash, beauty wash, milky lotion, cream, gel, essence, facial pack or mask. In addition, in the case of makeup cosmetics, the external preparation can be widely applied to forms such as foundation, or in the case of toiletry products, can be widely applied to forms such as body soap or hand soap. Moreover, in the case of quasi drugs, the external preparation can be widely applied to forms such as various types of ointments. The forms able to be adopted by an external preparation containing the elastase inhibitor of the present invention are not limited to these drug forms and product forms.

Moreover, the elastase inhibitor of the present invention can also be applied as a respiratory organ drug, drugs such as an acute lung disorder or acute respiratory distress syndrome drug, or an acute therapeutic agent such as an organ disorder drug.

The elastase inhibitor of the present invention can be formulated into various forms in the aforementioned applications using ordinary methods, examples of which include powders, granules, ampules, injections and isotonic solutions. Namely, in the case of preparing a solid preparation for oral administration, the elastase inhibitor of the present invention can be formulated into tablets, coated tablets or capsules and the like after adding a vehicle and further adding a binder, wetting agent, disintegration agent, surfactant, lubricant, dispersant, corrective or odor improving agent and the like as necessary.

Examples of vehicles used include lactose, glucose, sorbitol, cornstarch and mannitol, examples of binders used include polyvinyl alcohol, polyvinyl ether, ethyl cellulose, gum arabic, gelatin, hydroxypropyl cellulose and polyvinyl pyrrolidone, examples of disintegration agents used include calcium carbonate, calcium citrate, dextrin, starch and powdered gelatin, examples of lubricants used include calcium carbonate, calcium citrate, talc and polyethylene glycol, and examples of colorants used include powdered cocoa, peppermint aromatic acid and peppermint oil. These tablets and granules may be suitably coated with a sugar coating, gelatin coating or other coating as necessary. In the case of preparing an injection preparation, the injection preparation may be prepared for subcutaneous injection, intramuscular injection or intravenous injection using ordinary methods by adding a pH adjuster, buffer, surfactant, solubilizing agent, solvent, stabilizer or preservative and the like as necessary.

In still another aspect of the present invention, the present invention provides the use of the elastase inhibitor relating to the present invention as an external skin preparation, and preferably a cosmetic. An external skin preparation can be used by locally applying, for example, to the skin of subjects in needs of inhibition and/or prevention of decreases in skin resiliency in order to inhibit and/or prevent such decreases in skin resiliency associated with denaturation and destruction of elastin due to excess expression of elastase caused by, for example, exposure to ultraviolet rays and aging. Moreover, the present application provides the use of the elastase inhibitor relating to the present invention for the treatment and/or prevention of elastase-related diseases, examples of which include joint diseases such as chronic rheumatoid arthritis or osteoarthritis, systemic inflammatory response syndrome, arteriosclerosis, acute lung disorders and acute respiratory distress syndrome. The elastase inhibitor of the present invention can be applied orally or parenterally to such subjects requiring inhibition and/or prevention of decreases in skin resiliency.

EXAMPLES

Although the following provides a detailed explanation of the present invention through examples thereof, the present invention is not limited to the following examples.

A solution containing 0.1 M HEPES and 0.5 M NaCl (pH 7.5) was used as a reaction buffer. Oxysuccinyl-$(Ala)_2$-Pro-Val-MCA (Peptide Institute Cat. No. 3153-v) was used for the elastase substrate and dissolved in DMSO to a concentration of 80 mM followed by diluting to 0.16 mM with the reaction buffer. Human leukocyte-derived elastase (Elastin Product Co., Inc. Cat No. CK828) was diluted to 5 µg/mL with the reaction buffer.

25 µL aliquots of the 0.16 mM elastase substrate were dispensed into the wells of a 96-well plate followed by the addition of 50 µL of each drug. Next, 25 µL of ice-cooled 5 µg/mL elastase were added and incubated for 60 minutes at 37° C. followed by measuring fluorescence at 460 nm at an exciting wavelength of 369 nm. Raspberry extract BG manufactured by Maruzen Pharmaceuticals was used for the raspberry extract, L-hydroxyproline manufactured by Kyowa Hakko was used for the hydroxyproline, and Biodyne EMPP™ manufactured by Arch Personal Care Products L.P. was used for the yeast extract. Raspberry extract BG is a 1,3-butyleneglycol (50% aqueous solution) extract of raspberry fruit.

The results are shown in FIG. 1. Significant, concentration-dependent elastase inhibitory effects were able to be confirmed with raspberry extract alone. On the other hand, elastase inhibitory effects were not demonstrated in the case of hydroxyproline alone.

It was extremely interesting to find that even though hydroxyproline does not demonstrate elastase inhibitory effects alone, when combined with the use of raspberry extract, it significantly enhanced the elastase inhibitory effects of the raspberry extract. Thus, the combined use of hydroxyproline was determined to be able to synergistically enhance elastase inhibitory effects of raspberry extract.

FIG. 2 shows elastase inhibitory effects in the case of respectively using raspberry extract (0.001% by weight as dry form), hydroxyproline (0.025% by weight as dry form) and yeast extract (0.001% by weight as dry form) alone, and the case of using them in combination (0.001% by weight, 0.025% by weight and 0.001% by weight as dry form, respectively). The raspberry extraction solvent, 1,3-butyleneglycol was used as a control. Combining the use of each drug demonstrated significantly higher elastase inhibitory effects than in the case of using each drug alone.

| Formulation Example 1 Cream | |
|---|---|
| (Components) | (wt %) |
| (1) Stearic acid | 3.0 |
| (2) Stearyl alcohol | 5.0 |
| (3) Isopropyl myristate | 18.0 |
| (4) Glycerin monostearic acid ester | 3.0 |
| (5) Propylene glycol | 10.0 |
| (6) L-hydroxyproline | 0.01 |
| (7) Raspberry extract (as dry form) | 0.001 |
| (8) Potassium hydroxide | 0.2 |
| (9) Sodium hydrogen sulfite | 0.01 |
| (10) Preservative | As suitable |
| (11) Fragrance | As suitable |
| (12) Ion exchange water | Balance |

(Production Method)

Propylene glycol, L-hydroxyproline, raspberry extract and potassium hydroxide are added to the ion exchange water and dissolved followed by heating and holding at 70° C. (aqueous phase). The other components are mixed, melted by heating and held at 70° C. (oily phase). The oily phase is gradually added to the aqueous phase and after all of the oily phase had been added, the reaction is briefly allowed to proceed while holding at that temperature. Subsequently, the mixture is uniformly emulsified with a homomixer followed by cooling to 30° C. while stirring well.

Formulation Example 2 Cream

| (Components) | (wt %) |
|---|---|
| (1) Stearic acid | 2.0 |
| (2) Stearyl alcohol | 7.0 |
| (3) Hydrogenated lanolin | 3.0 |
| (4) Squalane | 4.0 |
| (5) 2-octyldecyl alcohol | 6.0 |
| (6) Polyoxyethylene (25 mol) cetyl alcohol ether | 3.0 |
| (7) Glycerin monostearic acid ester | 2.0 |
| (8) Propylene glycol | 6.0 |
| (9) L-hydroxyproline | 0.02 |
| (10) Present elastase inhibitor | |
| Raspberry extract (as dry form) | 0.005 |
| Yeast extract (as dry form) | 0.001 |
| (11) Sodium hydrogen sulfite | 0.03 |
| (12) Ethyl p-hydroxybenzoate | 0.3 |
| (13) Fragrance | As suitable |
| (14) Ion exchange water | Balance |

(Production Method)

Propylene glycol is added to the ion exchange water followed by heating and holding at 70° C. (aqueous phase). The other components are mixed, melted by heating and held at 70° C. (oily phase). The oily phase is gradually added to the aqueous phase and preliminarily emulsified followed by uniformly emulsifying with a homomixer and cooling to 30° C. while stirring well.

Formulation Example 3 Milky Lotion

| (Components) | (wt %) |
|---|---|
| (1) Stearic acid | 2.5 |
| (2) Cetyl alcohol | 1.5 |
| (3) Vaseline | 5.0 |
| (4) Liquid paraffin | 10.0 |
| (5) Polyoxyethylene (10 mol) monooleic acid ester | 2.0 |
| (6) Polyethylene glycol 1500 | 3.0 |
| (7) Triethanolamine | 1.0 |
| (8) Carboxyvinyl polymer | 0.05 |
| (9) Present elastase inhibitor | |
| L-hydroxyproline | 0.003 |
| Raspberry extract (as dry form) | 0.005 |
| (10) Sodium hydrogen sulfite | 0.01 |
| (11) Ethyl p-hydroxybenzoate | 0.3 |
| (12) Fragrance | As suitable |
| (13) Ion exchange water | Balance |

(Production Method)

Carboxyvinyl polymer is dissolved in a small amount of ion exchange water (A phase). Polyethylene glycol 1500 and triethanolamine are added to the remaining ion exchange water followed by dissolving by heating and holding at 70° C. (aqueous phase). The other components are mixed, melted by heating and held at 70° C. (oily phase). The oily phase is added to the aqueous phase and preliminarily emulsified followed by adding the A phase, uniformly emulsifying with a homomixer and cooling to 30° C. while stirring well following emulsification.

Formulation Example 4 Milky Lotion

| (Components) | (wt %) |
|---|---|
| (1) Microcrystalline wax | 1.0 |
| (2) Beeswax | 2.0 |
| (3) Lanolin | 20.0 |
| (4) Liquid paraffin | 10.0 |
| (5) Squalane | 5.0 |
| (6) Sorbitan sesquioleic acid ester | 4.0 |
| (7) Polyoxyethylene (20 mol) sorbitan monooleic acid ester | 1.0 |
| (8) Propylene glycol | 7.0 |
| (9) Present elastase inhibitor | |
| L-hydroxyproline | 0.01 |
| Raspberry extract (as dry form) | 0.001 |
| Yeast extract (as dry form) | 0.005 |
| (10) Rose hip leaf extract | 0.05 |
| (11) Sodium hydrogen sulfite | 0.01 |
| (12) Ethyl p-hydroxybenzoate | 0.3 |
| (13) Fragrance | As suitable |
| (14) Ion exchange water | Balance |

(Production Method)

Propylene glycol is added to the ion exchange water followed by heating and holding at 70° C. (aqueous phase). The other components are mixed, melted by heating and held at 70° C. (oily phase). The oily phase is gradually added to the aqueous phase while stirring and uniformly emulsified with a homomixer. The emulsion is cooled to 30° C. while stirring well following emulsification.

Formulation Example 5 Beauty Essence

| (Components) | (wt %) |
|---|---|
| (A Phase) | |
| (1) Ethyl alcohol (95%) | 10.0 |
| (2) Polyoxyethyene (20 mol) octyldodecanol | 1.0 |
| (3) Pantothenyl ethyl ether | 0.1 |
| (4) Present elastase inhibitor | |
| L-hydroxyproline | 0.001 |
| Raspberry extract (as dry form) | 0.001 |
| (5) Methyl p-hydroxybenzoate | 0.15 |
| (B Phase) | |
| (6) Potassium hydroxide | 0.1 |
| (C Phase) | |
| (7) Glycerin | 5.0 |
| (8) Dipropylene glycol | 10.0 |
| (9) Sodium hydrogen sulfite | 0.03 |
| (10) Carboxyvinyl polymer | 0.2 |
| (11) Purified water | Balance |

(Production Method)

The A phase and C phase are respectively uniformly dissolved followed by adding the A phase to the C phase and solubilizing. Next, the B phase is added followed by filling.

Formulation Example 6 Beauty Wash

| (Components) | (wt %) |
|---|---|
| (1) Ethanol | 5.0 |
| (2) Glycerin | 0.5 |
| (3) Dipropylene glycol | 2.0 |
| (4) 1,3-butyleneglycol | 5.5 |
| (5) Citric acid | 0.02 |
| (6) Sodium citrate | 0.08 |
| (7) Sodium hexametaphosphate | 0.03 |
| (8) Hydroxypropyl-β-cyclodextrin | 0.1 |

-continued

| Formulation Example 6 Beauty Wash | |
|---|---|
| (Components) | (wt %) |
| (9) Present elastase inhibitor | |
|     L-hydroxyproline | 0.003 |
|     Raspberry extract (as dry form) | 0.003 |
| (10) Lavender oil | 0.1 |
| (11) Sodium alginate | 0.001 |
| (12) Purified water | Balance |

(Production Method)

Components (1) to (12) are mixed and dissolved in accordance with ordinary methods to obtain a beauty wash.

The invention claimed is:

1. An elastase inhibitor containing as active ingredients thereof effective amounts of a raspberry fruit extract and hydroxyproline, wherein the raspberry fruit extract is obtained by extracting fruit of raspberry with a solution comprising 1,3 - butylene glycol.

2. The elastase inhibitor according to claim 1, wherein the hydroxyproline is L-hydroxyproline.

3. The elastase inhibitor according to claim 1, further containing a yeast extract.

4. The elastase inhibitor according to claim 3, wherein the yeast extract is prepared from yeast which has been cultured in a nutrient medium containing glycosaminoglycan, and which has been subjected to ultraviolet radiation, hydrogen peroxide treatment or both.

5. An external skin preparation containing the elastase inhibitor according to claim 1.

6. The external skin preparation according to claim 5, which is a cosmetic.

* * * * *